US008192419B2

United States Patent
Li et al.

(10) Patent No.: US 8,192,419 B2
(45) Date of Patent: Jun. 5, 2012

(54) CATHETER ASSEMBLY INCLUDING INTERNAL BOLSTER

(75) Inventors: Changqing Li, Ellettsville, IN (US); Gene McCallister, Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/974,363

(22) Filed: Dec. 21, 2010

(65) Prior Publication Data

US 2011/0092912 A1     Apr. 21, 2011

Related U.S. Application Data

(62) Division of application No. 11/389,801, filed on Mar. 27, 2006, now abandoned.

(51) Int. Cl.
*A61M 31/00*     (2006.01)
*A61M 5/32*     (2006.01)
*A61M 25/00*     (2006.01)

(52) U.S. Cl. ............... 604/500; 604/174; 604/523

(58) Field of Classification Search ............... 604/96.01, 604/174, 104, 105, 106, 107, 164, 175, 194, 604/198
See application file for complete search history.

(56) References Cited

U.S. PATENT DOCUMENTS

| | | | |
|---|---|---|---|
| 3,490,456 A * | 1/1970 | Kortum | 604/106 |
| 4,393,873 A | 7/1983 | Nawash et al. | |
| 4,623,348 A | 11/1986 | Feit | |
| 4,861,334 A | 8/1989 | Nawaz | |
| 4,900,306 A | 2/1990 | Quinn et al. | |
| 5,041,085 A | 8/1991 | Osborne et al. | |
| 5,112,310 A * | 5/1992 | Grobe | 604/175 |
| 5,167,627 A | 12/1992 | Clegg et al. | |

(Continued)

FOREIGN PATENT DOCUMENTS

WO     98/15309 A1     4/1998

OTHER PUBLICATIONS

European Patent Office, International Search Report in International Application No. PCT/US2007/007469, dated Aug. 29, 2007.

*Primary Examiner* — Kevin C Sirmons
*Assistant Examiner* — William Carpenter
(74) *Attorney, Agent, or Firm* — Kenyon & Kenyon LLP

(57) ABSTRACT

A catheter assembly including an internal bolster. According to one embodiment, the catheter assembly includes a medical catheter preferably made of extruded silicone rubber. The catheter is shaped to include a cylindrical wall defining a primary longitudinal bore. A plurality of secondary longitudinal bores is provided in the cylindrical wall, the secondary bores being evenly spaced around the primary bore. The assembly also includes a plurality of identical resilient members collectively forming an anchor at a first end of the catheter. Each resilient member comprises a resilient wire and a protective jacket. Each wire is made of a shape-memory material and is reversibly transformable between a spiral shape, when at rest, and a straightened shape, when forcibly unfurled. One end of each wire is disposed within a secondary bore of the catheter, with the remainder of each wire extending out from the catheter. Each jacket is preferably made of silicone rubber and encapsulates all of the length of its wire, except for the small portion of the wire inserted into the bore.

15 Claims, 12 Drawing Sheets

U.S. PATENT DOCUMENTS

| | | | |
|---|---|---|---|
| 5,267,960 A | 12/1993 | Hayman et al. | |
| 5,279,564 A * | 1/1994 | Taylor | 604/104 |
| 5,358,488 A | 10/1994 | Suriyapa | |
| 5,391,159 A | 2/1995 | Hirsch et al. | |
| 5,509,900 A * | 4/1996 | Kirkman | 604/104 |
| 5,599,291 A | 2/1997 | Balbierz et al. | |
| 5,769,821 A | 6/1998 | Abrahamson et al. | |
| 6,030,364 A | 2/2000 | Durgin et al. | |
| 6,402,722 B1 | 6/2002 | Snow et al. | |
| 6,482,178 B1 | 11/2002 | Andrews et al. | |
| 6,626,859 B2 | 9/2003 | von Segesser | |
| 2004/0059293 A1 | 3/2004 | Chu et al. | |
| 2005/0216028 A1 | 9/2005 | Hart et al. | |
| 2006/0229553 A1 | 10/2006 | Hammack et al. | |

* cited by examiner

CATHETER ASSEMBLY INCLUDING INTERNAL BOLSTER

CROSS REFERENCE TO RELATED APPLICATION

This application is a divisional of U.S. application Ser. No. 11/389,801, filed Mar. 27, 2006, which is hereby incorporated by reference in its entirety.

BACKGROUND OF THE INVENTION

The present invention relates generally to medical catheters and relates more particularly to medical catheters of the type having an internal bolster disposed at one end of said medical catheter for retaining said end of said medical catheter within a patient.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. (A less common approach involves jejunostomy, i.e., the creating of a feeding tract or stoma leading into the patient's jejunum.) Feeding is then typically performed by administering food through a catheter or feeding tube that has been inserted into the feeding tract, with one end of the feeding tube extending into the stomach and being retained therein by an internal anchor or bolster and the other end of the feeding tube extending through the abdominal wall and terminating outside of the patient.

Although gastrostomies were first performed surgically, most gastrostomies are now performed using percutaneous endoscopy and result in the implantation in the patient of a feeding tube/internal bolster assembly (said feeding tube/internal bolster assembly also commonly referred to as a percutaneous endoscopic gastrostomy (PEG) device). Two of the more common percutaneous endoscopic techniques for implanting a PEG device in a patient are "the push method" (also known as "the Sacks-Vine method") and "the pull method" (also known as "the Gauderer-Ponsky method"). Information regarding the foregoing two methods may be found in the following patents, all of which are incorporated herein by reference: U.S. Pat. No. 5,391,159, inventors Hirsch et al., which issued Feb. 21, 1995; U.S. Pat. No. 5,167,627, inventors Clegg et al., which issued Dec. 1, 1992; U.S. Pat. No. 5,112,310, inventor Grobe, which issued May 12, 1992; U.S. Pat. No. 4,900,306, inventors Quinn et al., which issued Feb. 13, 1990; and U.S. Pat. No. 4,861,334, inventor Nawaz, which issued Aug. 29, 1989.

In addition to the above-described endoscopic techniques for implanting PEG devices, there also exist direct percutaneous techniques. Typically, such direct percutaneous techniques involve (i) inserting an endoscope into the patient and, through transillumination, identifying a desired insertion site; (ii) using sutures or T-fasteners, placed one at a time, to secure the abdominal wall to the stomach wall in a plurality of locations surrounding the future insertion site; (iii) using a scalpel to make an incision at the insertion site; (iv) using a series of dilators to enlarge the insertion site opening until said opening is large enough to pass therethrough the internal bolster at the distal end of a gastrostomy tube; and (v) sliding an external bolster over the proximal end of the gastrostomy tube down to skin level over the T-fastener wires or sutures.

Other direct percutaneous techniques are disclosed in the following patents and published patent applications, all of which are incorporated herein by reference: U.S. Pat. No. 6,030,364, inventors Durgin et al., which issued Feb. 29, 2000; U.S. Pat. No. 6,402,722, inventors Snow et al., which issued Jun. 11, 2002; and U.S. Published Patent Application No. US-2004-0059293-A1, which was published Mar. 25, 2004.

SUMMARY OF THE INVENTION

It is an object of the present invention to provide a novel catheter assembly.

Therefore, according to one aspect of the present invention, there is provided a catheter assembly comprising (a) a catheter, said catheter having a first end and a second end; and (b) an internal bolster disposed at said first end of said catheter, said internal bolster comprising a plurality of resilient members collectively forming an anchor reversibly transformable between a radially expanded state and a radially condensed state.

According to one embodiment, the catheter assembly includes a medical catheter preferably made of extruded silicone rubber. The catheter is shaped to include a cylindrical wall defining a primary longitudinal bore. A plurality of secondary longitudinal bores are provided in the cylindrical wall, the secondary bores being evenly spaced around the primary bore. The assembly also includes a plurality of identical resilient members collectively forming an anchor at a first end of the catheter. Each resilient member comprises a resilient wire and a protective jacket. Each wire is preferably made of a shape-memory material and is reversibly transformable between a spiral shape that extends radially outwardly and towards the second end of the catheter, when at rest, and a straightened shape that extends away from the second end of the catheter, when forcibly unfurled. One end of each wire is disposed within a secondary bore of the catheter, with the remainder of each wire extending out from the catheter. Each jacket is preferably made of silicone rubber and encapsulates all of the length of its wire, except for the small portion of the wire inserted into the bore.

According to another embodiment, each resilient member is made by insert-molding the protective jacket over the entirety of the wire and then insert-molding the catheter around one end of each of the plurality of resilient members.

According to still another embodiment, there is provided a unitary insert shaped to include an annular base portion and a plurality of resilient wires extending from the annular base portion. Silicone rubber or a similarly suitable material is then insert-molded over the insert to cover the resilient wires and to define an associated catheter.

According to yet another embodiment, the resilient members do not include an embedded wire, the catheter assembly instead being a unitary structure made entirely of silicone rubber or a similarly suitable material.

According to another aspect of the invention, there is provided a catheter assembly comprising (a) a catheter, said catheter having a first end and a second end; and (b) a plurality of resilient members disposed at said first end of said catheter, each of said resilient members being reversibly transformable between a spiral shape, when at rest, and a straightened shape, when forcibly unfurled.

According to yet another aspect of the invention, there is provided a kit for use in implanting a catheter assembly in a patient, said kit comprising (a) a catheter assembly, said catheter assembly comprising (i) a catheter, said catheter having a first end and a second end, and (ii) an internal bolster disposed at said first end of said catheter, said internal bolster comprising a plurality of resilient members, each of said resilient members being reversibly transformable between a spiral shape, when at rest, and a straightened shape, when forcibly unfurled, said spiral shape extending radially outwardly from said catheter and towards said second end of said catheter; and (b) a delivery device, said delivery device being a tubular member appropriately dimensioned to be inserted over said catheter assembly from said second end of said catheter and to unfurl said resilient members.

For purposes of the present specification and claims, various relational terms like "top," "bottom," "proximal" and "distal" are used to describe the present invention when said invention is positioned in or viewed from a given orientation. It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration certain embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Figure 1A:
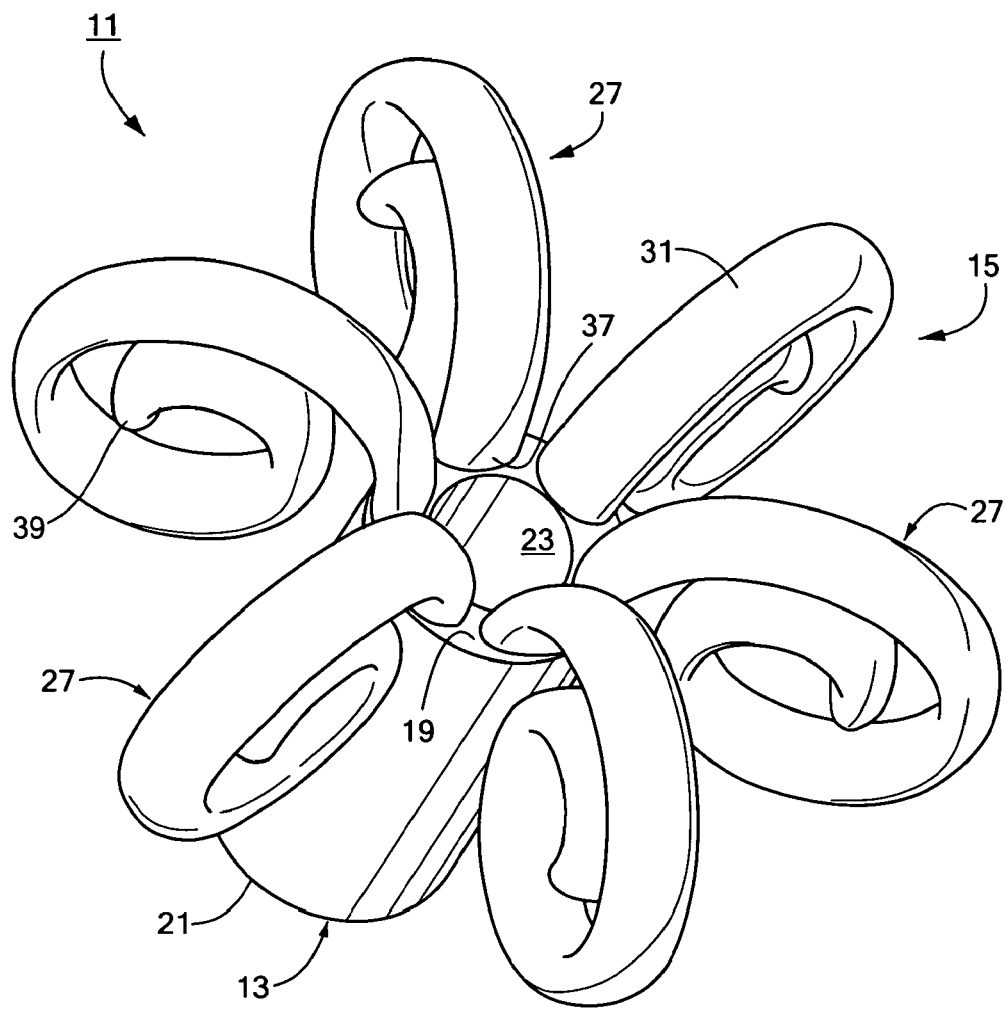
FIGS. 1(a) and 1(b) are perspective and longitudinal section views, respectively, of a first embodiment of a catheter assembly constructed according to the teachings of the present invention, the internal bolster of the catheter assembly being shown in an expanded state.
Figure 1B:
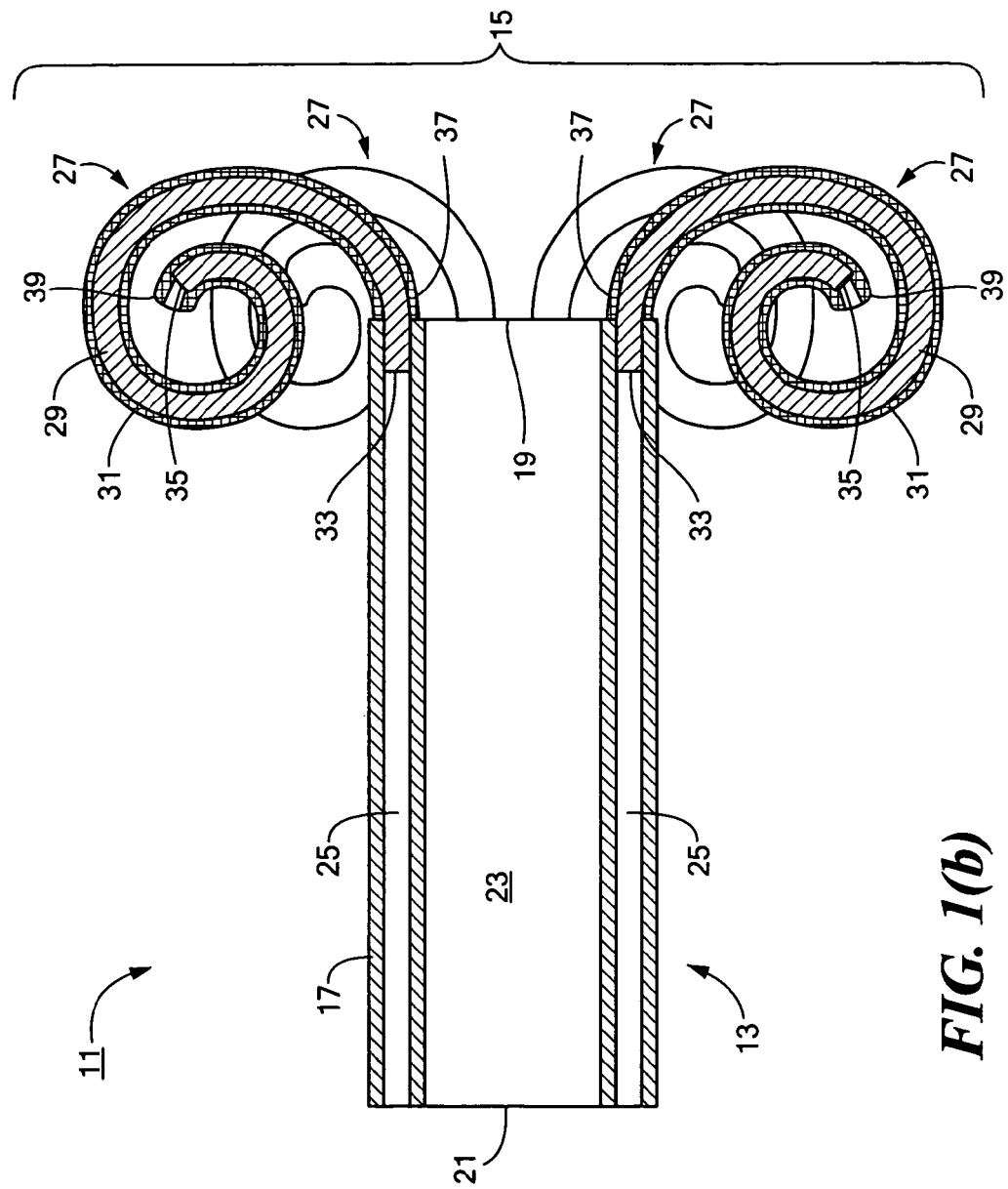

Referring now to FIGS. 1(a) and 1(b), there are shown perspective and longitudinal section views, respectively, of a first embodiment of a catheter assembly constructed according to the teachings of the present invention, said catheter assembly being shown with its internal bolster in an expanded state, said catheter assembly being represented generally by reference numeral 11.

Catheter assembly 11 includes a medical catheter 13 and an internal bolster 15.

Catheter 13 is an elongated, unitary, tubular structure preferably made of a flexible, biocompatible material, such as silicone rubber. Catheter 13, which is preferably made by extrusion, is shaped to include a cylindrical wall 17 terminating in a first end 19 and in a second end 21, cylindrical wall 17 coaxially surrounding and defining a primary longitudinal bore 23. As will be discussed further below, primary longitudinal bore 23 is preferably used to convey fluids, such as food and/or medications, to a patient in need thereof. A plurality of secondary longitudinal bores 25 are provided in cylindrical wall 17, bores 25 being evenly spaced around the periphery of primary longitudinal bore 23. As will be discussed further below, secondary longitudinal bores 25 are used in the mounting of internal bolster 15 to catheter 13. A series of ruler markings (not shown) are printed on catheter 13 and extend several inches from first end 19 in the direction of second end 21 to facilitate the cutting of catheter 13 to a desired length after catheter 13 has been implanted in a patient.

Internal bolster 15 comprises a plurality of identical resilient members 27 disposed at first end 19 of catheter 13, resilient members 27 collectively functioning as a reversibly transformable anchor. In the present embodiment, this anchor is in the form of an iris diaphragm; however, the anchor may take forms other than that of an iris diaphragm. Each resilient member 27 comprises a resilient wire 29 and a protective jacket 31. Each wire 29 is made of a material that permits its reversible transformation between a spiral shape, when relaxed, and a straightened shape, when forcibly unfurled. Examples of the materials that may be used to make wire 29 include shape-memory materials, such as nitinol (a nickel/titanium alloy), and elastomeric materials. Each wire 29 has a first end 33 and a second end 35. The first end 33 of each wire 29 is disposed within a corresponding bore 25 of catheter 13, with the remainder of each wire 29 extending out from first end 19 of catheter 13. Each jacket 31, which is preferably made of silicone rubber or a similarly flexible, biocompatible material, encapsulates most of the length of wire 29, except for the small portion of wire 29 inserted into bore 25. Each jacket 31 has a first end 37 and a second end 39. First end 37 of jacket 31 is in contact with first end 19 of catheter 13, and second end 39 of jacket 31 extends for a distance beyond second end 35 of wire 29 so that no part of wire 29 is exposed to the patient. Preferably, each member 27 is made by (i) inserting first end 33 of wire 29 into bore 25, first end 33 fitting within bore 25 by an interference fit, (ii) straightening wire 29, and (iii) insert-molding jacket 31 around the exposed portion of straightened wire 29 and to catheter 13.

As can be seen, members 27 are oriented relative to catheter 13 so that (i) when each member 27 is in a relaxed state, said member 27 spirals radially outwardly relative to catheter 13 and in the direction of second end 21 of catheter 13 and (ii) when each member 27 is in an unfurled state, said member 27 extends parallel to the longitudinal axis of catheter 13, with its free end extending away from first end 19 of catheter 13 in the direction opposite to second end 21.

It should be understood that, although the present embodiment includes six resilient members 27 spaced around first end 19 of catheter 13, there could be as few as two resilient members 27 spaced around first end 19 of catheter 13 or more than six resilient members 27 spaced around first end 19 of catheter 13. In addition, it should be understood that resilient members 27 are not limited to assuming, when at rest, the particular spiral shape shown in FIGS. 1(a) and 1(b). Rather, resilient members 27 may instead form a looser curl, a tighter curl, a longer curl, a shorter curl, a fatter curl, a thinner curl, etc. In addition, there may be alternate geometries to spirals, such as balled or knotted members, that may have improved strength. Moreover, there may be various types of resilient members disposed around the catheter.

Referring now to FIGS. 2(a) through 2(e), there is schematically shown the manner in which catheter assembly 11 may be implanted in a patient. (For illustrative purposes, catheter assembly 11 is herein shown as an initial placement PEG device being implanted in the stomach of a patient; however, it is to be understood that catheter assembly 11 may be either an initial placement device or a replacement device and may be implanted in the stomach of a patient or at other locations within a patient where the delivery and/or drainage of fluids is desirable.) First, referring to FIG. 2(a), distal end D of endoscope E is inserted into the stomach of a patient, and an intense light source L disposed within endoscope E is used to transilluminate the stomach wall S and the abdominal wall A of the patient so as to indicate externally a desired incision site. Preferably, while the aforementioned transillumination process is conducted, a supply of gas is used to inflate the patient's stomach, thereby distending the stomach and facilitating the transillumination process.

Figure 2A:
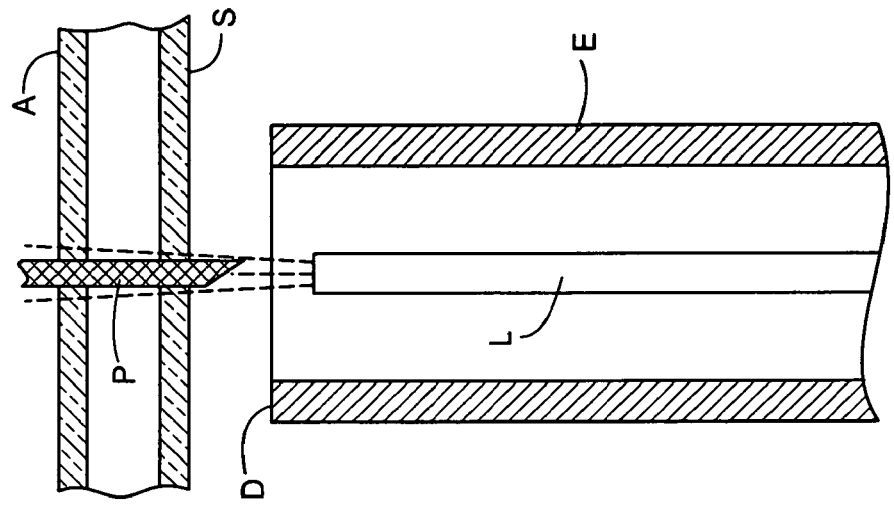
FIG. 2(a) through 2(e) are fragmentary schematic views, partly in section, illustrating the manner in which the catheter assembly of FIGS. 1(a) and 1(b) may be implanted in a patient in accordance with the teachings of the present invention.
Figure 2B:
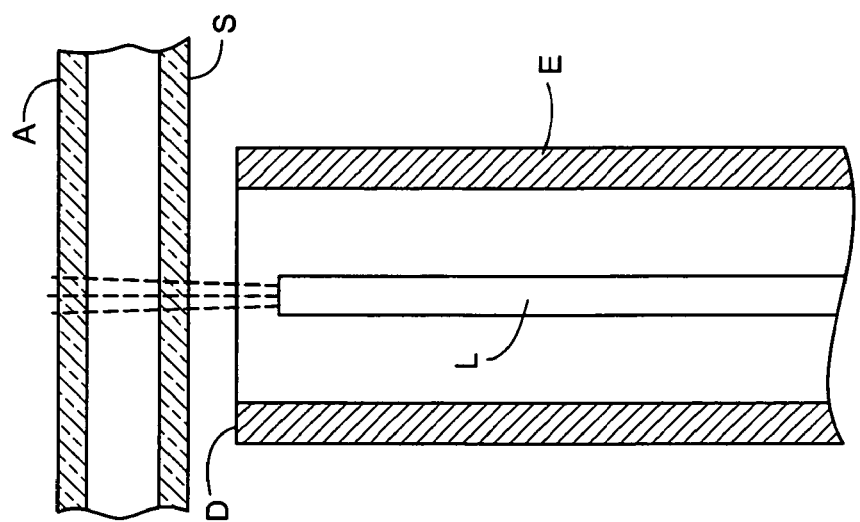
Figure 2D:
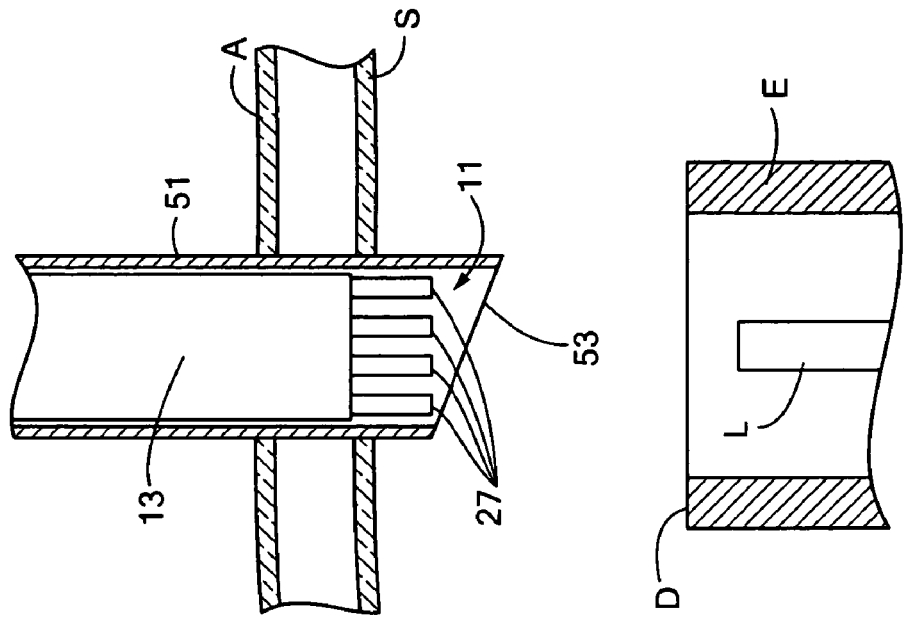
Figure 2C:
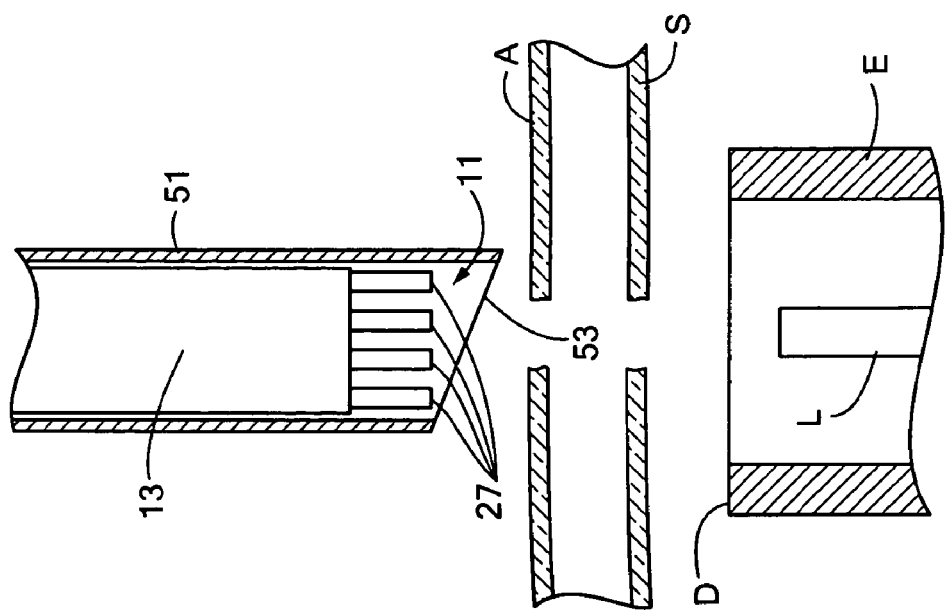
Figure 2E:
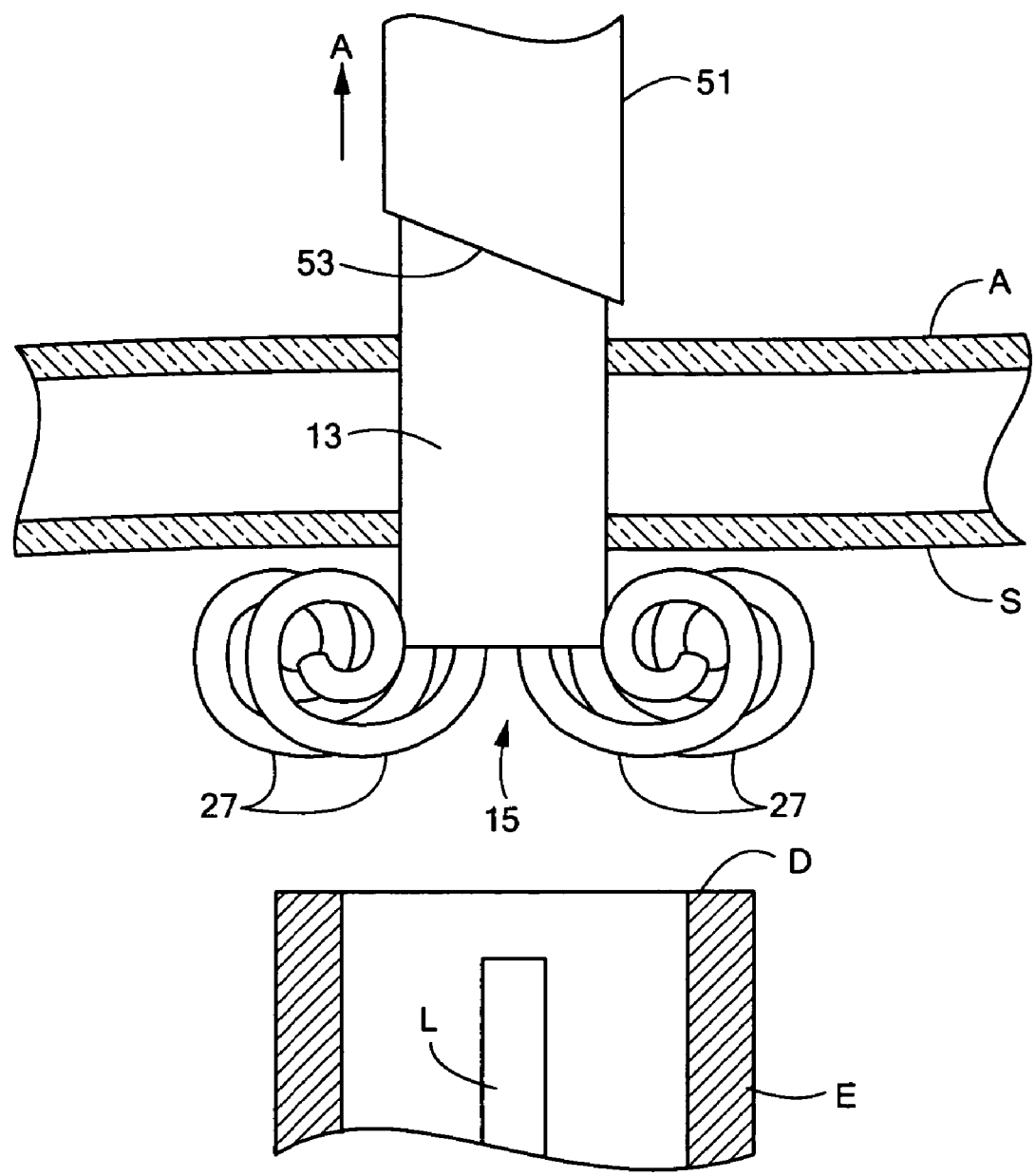

Next, as seen in FIG. 2(b), using a scalpel P, incisions are made in the abdominal wall A and in the stomach wall S of the patient at the desired incision site. Next, as seen in FIG. 2(c), assembly 11 (which is not shown in section) is loaded into a delivery device 51, delivery device 51 being a tubular member whose inner diameter is appropriately dimensioned to receive assembly 11 and to unfurl members 27 to their respective straightened states. As shown in the present embodiment, delivery device 51 preferably has a sharpened distal end 53 to facilitate its insertion through abdominal wall A and stomach wall S. Next, as seen in FIG. 2(d), the distal ends of delivery device 51 and assembly 11 are inserted through abdominal wall A and stomach wall S at the incision site. It should be noted that, in addition to being used to straighten members 27, delivery device 51 also provides stiffening support to catheter 13, which possesses limited inherent stiffness and, therefore, cannot easily be inserted by itself through the incision site. Next, as seen in FIG. 2(e), while keeping assembly 11 stationary, delivery device 51 is withdrawn from the patient in the direction indicated by arrow A. The removal of device 51 from members 27 permits members 27 to assume their relaxed, expanded states, thereby causing catheter 13 to be anchored within the stomach of the patient. The implanted device may then be endoscopically checked for proper placement, cut to a desired length, and secured to an external bolster, Y-port and/or clamp in the conventional manner. Food and/or medications may then be delivered to the patient through the central bore of catheter 13.

When catheter assembly 11 is thus implanted in a patient, catheter assembly 11 is preferably able to withstand a pull force of about 14 pounds applied to second end 21 of catheter 13, without permitting assembly 11 to be withdrawn from the patient.

To safely remove assembly 11 from a patient, one may insert delivery device 51 over the implanted assembly 11, thereby causing members 27 to be unfurled, and may then remove delivery device 51 and assembly 11 together from the patient.

Figure 3A:
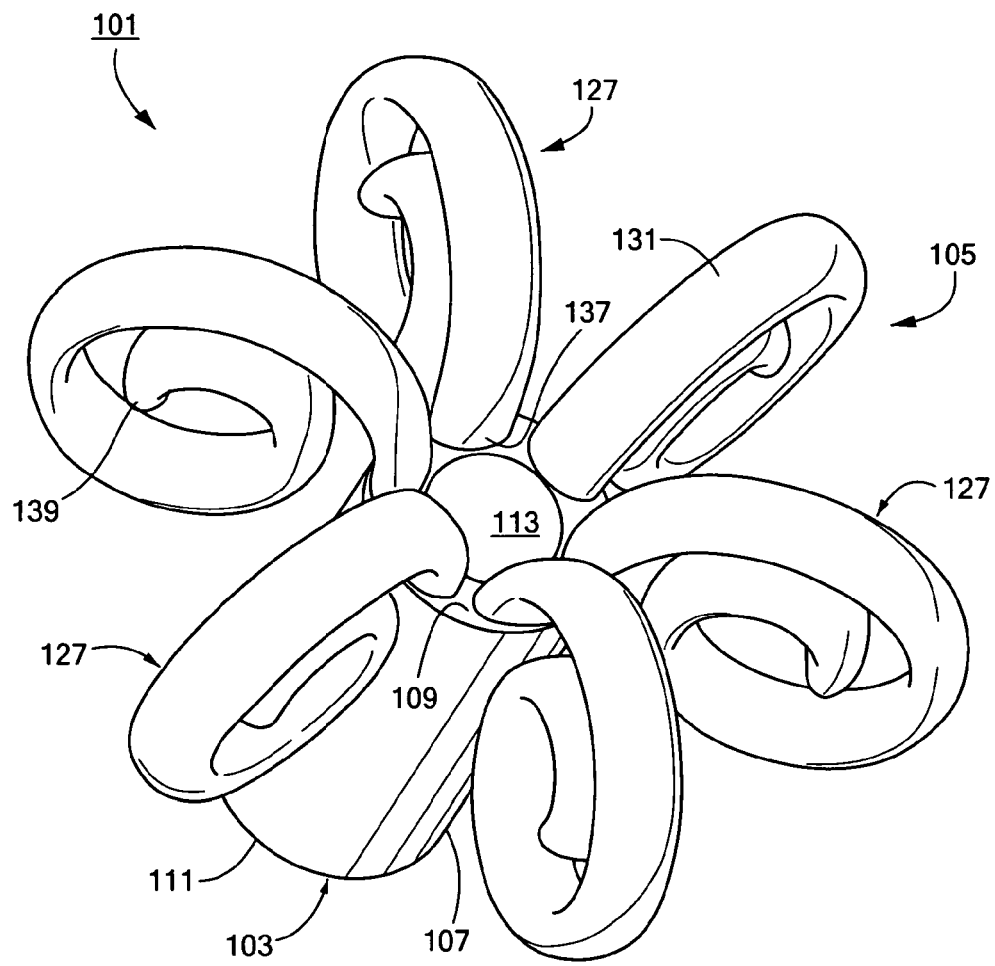
FIGS. 3(a) and 3(b) are perspective and longitudinal section views, respectively, of a second embodiment of a catheter assembly constructed according to the teachings of the present invention, the internal bolster of the catheter assembly being shown in an expanded state.
Figure 3B:
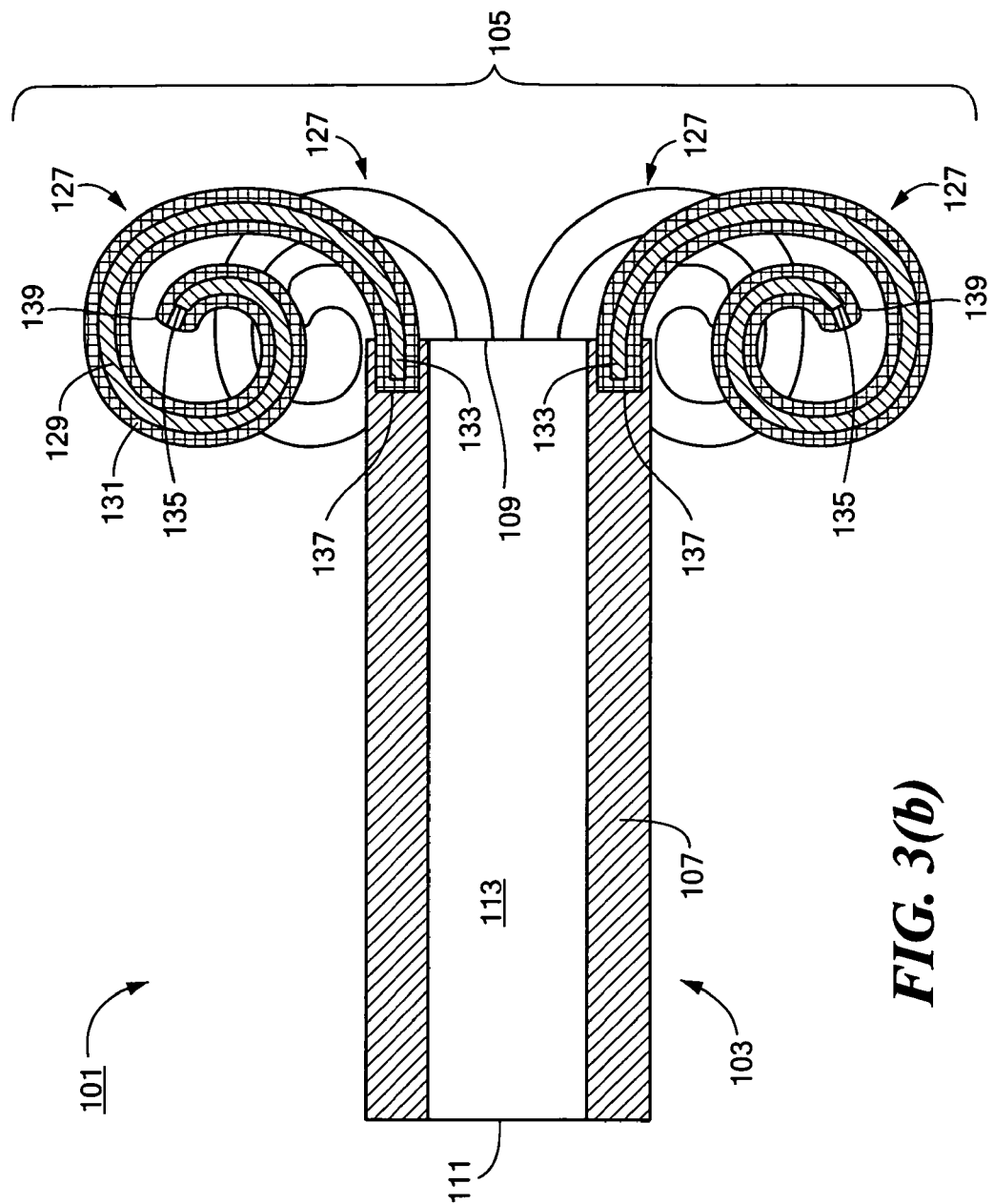

Referring now to FIGS. 3(a) and 3(b), there are shown perspective and longitudinal section views, respectively, of a second embodiment of a catheter assembly constructed according to the teachings of the present invention, the internal bolster of the catheter assembly being shown in an expanded state, said catheter assembly being represented generally by reference numeral 101.

Assembly 101 includes a catheter 103 and an internal bolster 105. Catheter 103 is an elongated, unitary, tubular structure preferably made of a flexible, biocompatible material, such as silicone rubber. Catheter 103 is shaped to include a cylindrical wall 107 terminating in a first end 109 and in a second end 111, cylindrical wall 107 coaxially surrounding and defining a longitudinal bore 113 adapted to convey fluids, such as food and/or medications, to a patient in need thereof. A series of ruler markings (not shown) are printed on catheter 103 and extend several inches from first end 109 in the direction of second end 111 to facilitate the cutting of catheter 103 to a desired length after catheter 103 has been implanted in a patient.

Internal bolster 105 comprises a plurality of identical resilient members 127 collectively forming a reversibly transformable anchor at first end 109 of catheter 103. In the present embodiment, this anchor is in the form of an iris diaphragm; however, the anchor may take forms other than that of an iris diaphragm. Each resilient member 127 comprises a resilient wire 129 and a protective jacket 131. Each wire 129 is made of a material that permits its reversible transformation between a spiral shape, when relaxed, and a straightened shape, when forcibly unfurled. Examples of the materials that may be used to make wire 129 include shape-memory materials, such as nitinol (a nickel/titanium alloy), and elastomeric materials. Each wire 129 has a first end 133 and a second end 135. Each jacket 131, which is preferably made of silicone rubber or a similarly flexible, biocompatible material, encapsulates the entire length of its wire 129. Each jacket 131 has a first end 137 and a second end 139.

Preferably, assembly 101 is made by insert-molding jacket 131 around each wire 129 to form each member 127 and then insert-molding catheter 103 around the first end 137 of the six members 127.

It should be understood that, although the present embodiment includes six resilient members 127 spaced around first end 109 of catheter 103, there could be as few as two resilient members 127 spaced around first end 109 of catheter 103 or more than six resilient members 127 spaced around first end 109 of catheter 103. In addition, it should be understood that resilient members 127 are not limited to assuming, when at rest, the particular spiral shape shown in FIGS. 3(a) and 3(b). Rather, resilient members 127 may instead form a looser curl, a tighter curl, a longer curl, a shorter curl, a fatter curl, a thinner curl, etc. In addition, there may be alternate geometries to spirals, such as balled or knotted members, that may have improved strength. Moreover, there may be various types of resilient members disposed around the catheter.

Assembly 101 may be implanted, used and removed in the same fashion as described above for assembly 11.

It should be understood that, instead of insert-molding catheter 103 around the first end 137 of the six members 127, one could simply bond the six members 127 to an end of a suitable medical catheter.

Figure 4A:
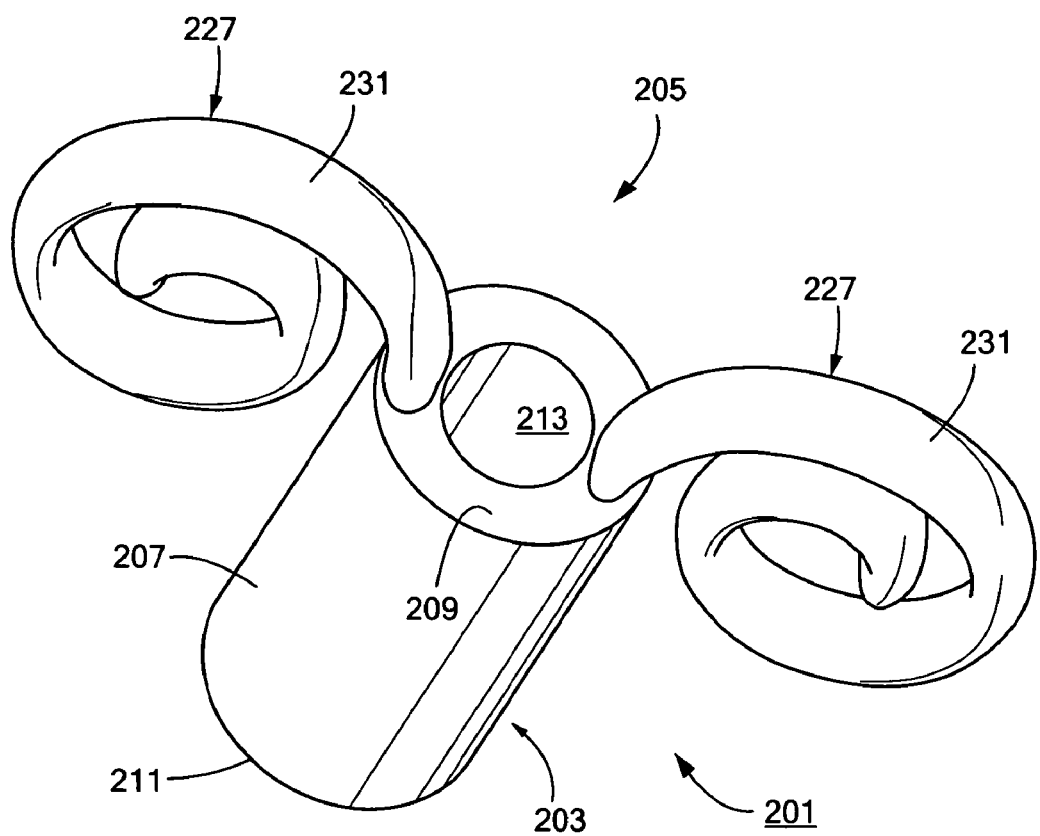
FIGS. 4(a) and 4(b) are perspective and longitudinal section views, respectively, of a third embodiment of a catheter assembly constructed according to the teachings of the present invention, the internal bolster of the catheter assembly being shown in an expanded state.
Figure 4B:
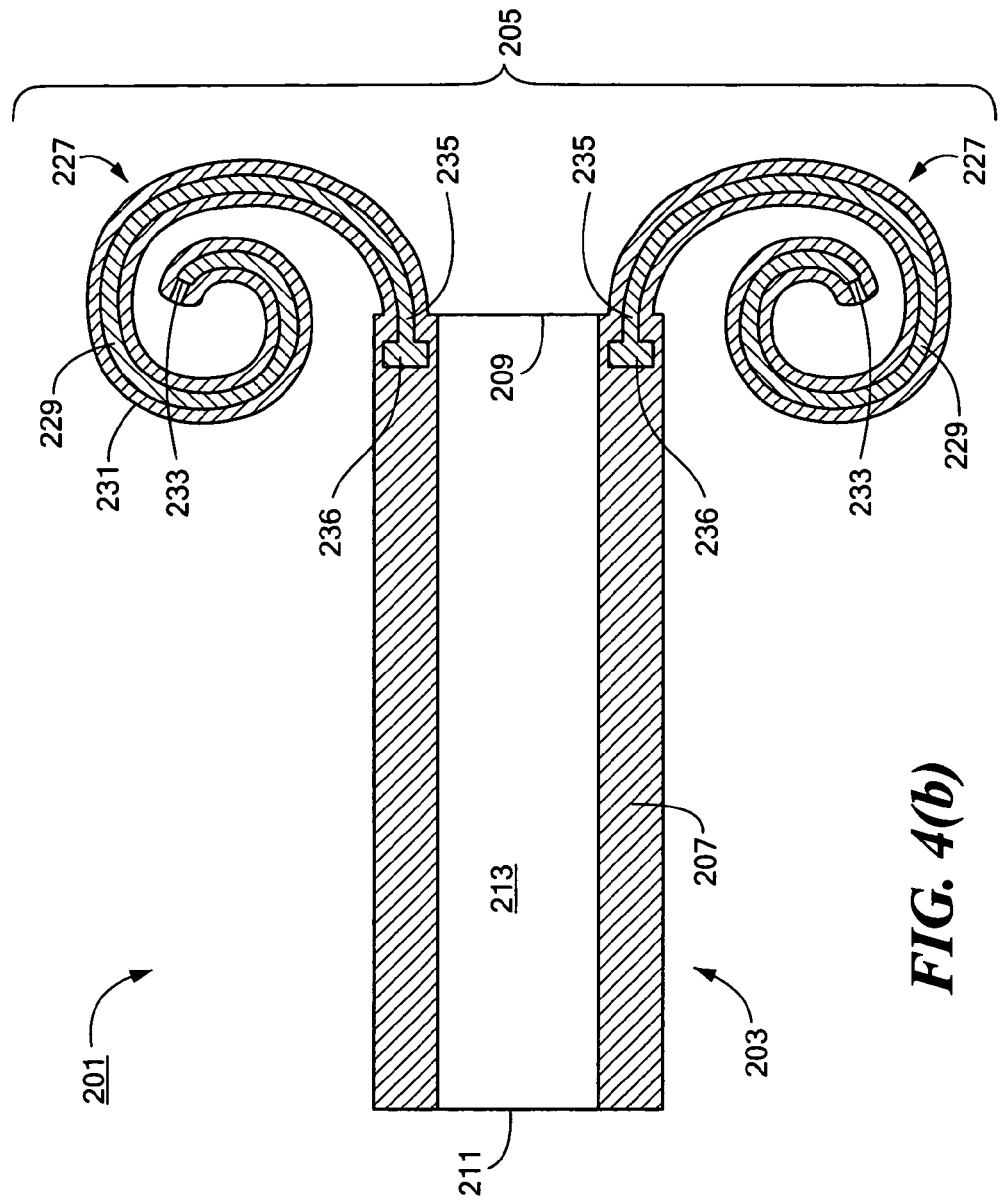

Referring now to FIGS. 4(*a*) and 4(*b*), there are shown perspective and longitudinal section views, respectively, of a third embodiment of a catheter assembly constructed according to the teachings of the present invention, the internal bolster of the catheter assembly being shown in an expanded state, said catheter assembly being represented generally by reference numeral 201.

Assembly 201 includes a catheter 203 and an internal bolster 205. Catheter 203 is an elongated, tubular structure made primarily of a flexible, biocompatible material, such as silicone rubber. Catheter 203 is shaped to include a cylindrical wall 207 terminating in a first end 209 and in a second end 211. Cylindrical wall 207 coaxially surrounds and defines a longitudinal bore 213 adapted to convey fluids, such as food and/or medications, to a patient in need thereof. A series of ruler markings (not shown) are printed on catheter 203 and extend several inches from first end 209 in the direction of second end 211 to facilitate the cutting of catheter 203 to a desired length after catheter 203 has been implanted in a patient.

Figure 5:
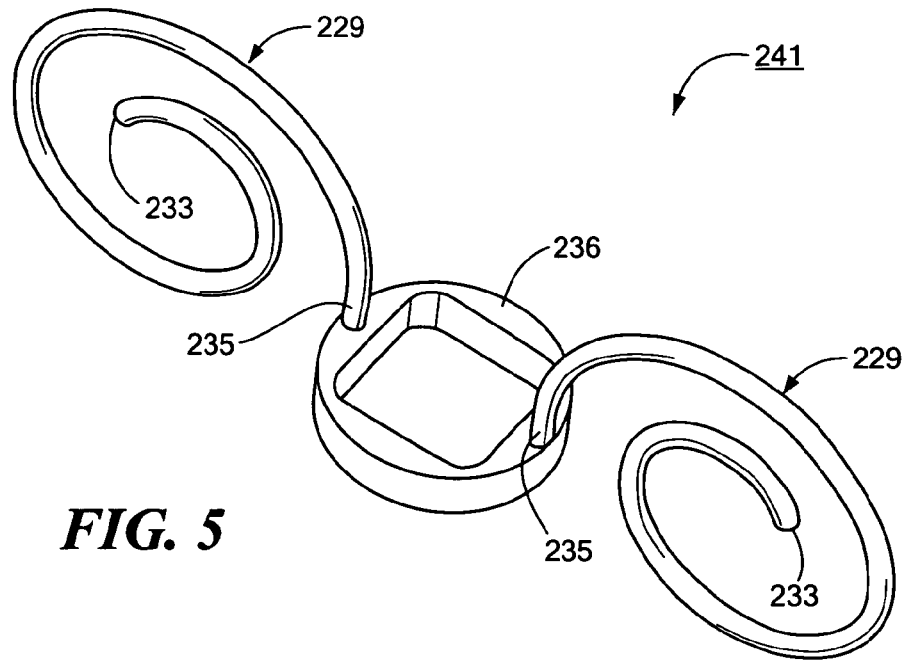
FIG. 5 is a perspective view of the wire insert of the catheter assembly of FIGS. 4(a) and 4(b)

Internal bolster 205 comprises a pair of identical resilient members 227 collectively forming a reversibly transformable anchor at first end 209 of catheter 203. In the present embodiment, this anchor is in the form of an iris diaphragm; however, the anchor may take forms other than that of an iris diaphragm. Each resilient member 227 comprises a resilient wire 229 and a protective jacket 231. Each wire 229 is made of a material that permits its reversible transformation between a spiral shape, when relaxed, and a straightened shape, when forcibly unfurled. Each wire 229 has a first end 233 and a second end 235. The second ends 235 of the two wires 229 are joined to a common annular base 236 to form a unitary insert 241, base 236 being embedded within cylindrical wall 207 of catheter 203 proximate to first end 209. (Insert 241 is shown separately in FIG. 5.) Each jacket 231, which is preferably made of silicone rubber or a similarly flexible, biocompatible material, encapsulates the entire length of its wire 229.

Preferably, assembly 201 is made by injection molding insert 241 and then insert-molding silicone rubber or the like over insert 241.

It should be understood that, although assembly 201 includes two resilient members 227, assembly 201 could be modified to include more than two resilient members 227. In addition, it should be understood that resilient members 227 are not limited to assuming, when at rest, the particular spiral shape shown in FIGS. 4(*a*) and 4(*b*). Rather, resilient members 227 may instead form a looser curl, a tighter curl, a longer curl, a shorter curl, a fatter curl, a thinner curl, etc. In addition, there may be alternate geometries to spirals, such as balled or knotted members, that may have improved strength. Moreover, there may be various types of resilient members disposed around the catheter.

Assembly 201 may be implanted, used and removed in the same fashion as described above for assembly 11.

Figure 6A:
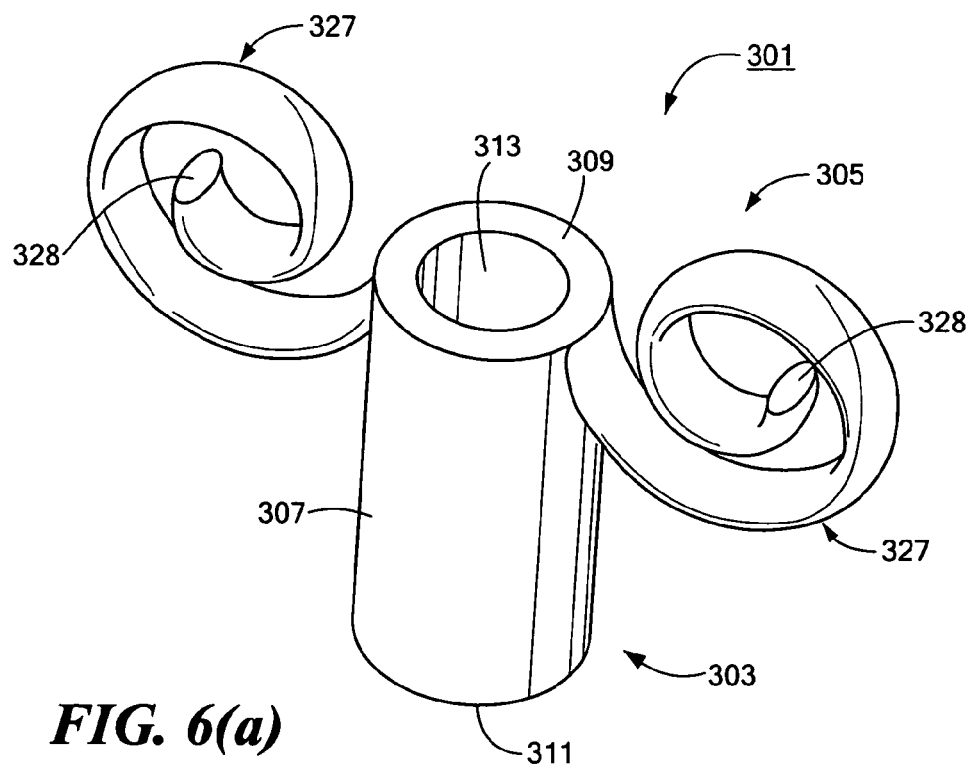
FIGS. 6(a) and 6(b) are perspective and longitudinal section views, respectively, of a fourth embodiment of a catheter assembly constructed according to the teachings of the present invention, the internal bolster of the catheter assembly being shown in an expanded state.
Figure 6B:
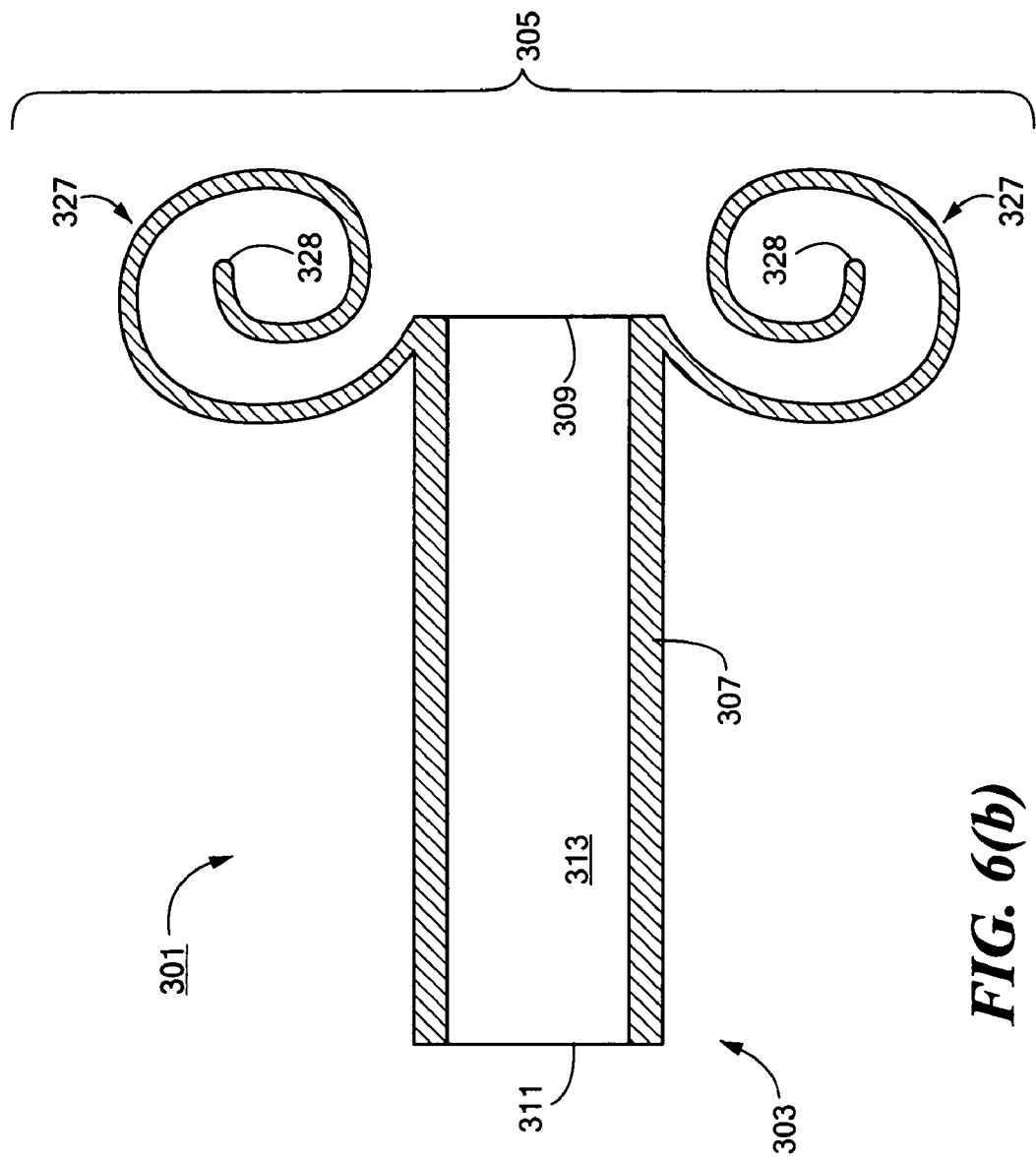
Figure 7:
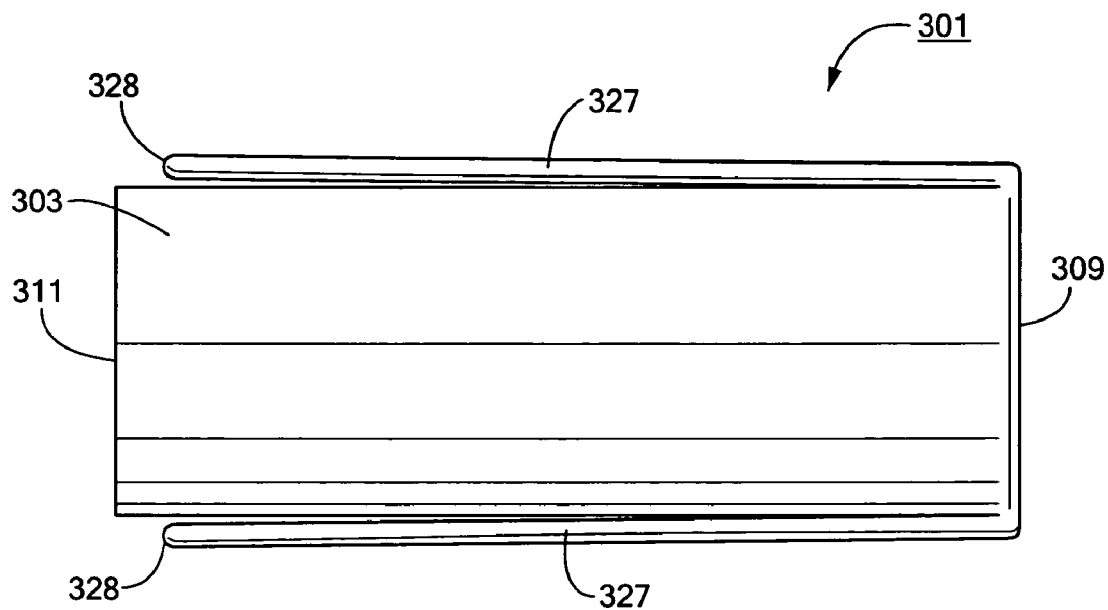
FIG. 7 is a side view of the catheter assembly of FIGS. 6(a) and 6(b), the internal bolster being shown in an unfurled state.

Referring now to FIGS. 6(*a*) and 6(*b*), there are shown perspective and longitudinal section views, respectively, of a fourth embodiment of a catheter assembly constructed according to the teachings of the present invention, the internal bolster of the catheter assembly being shown in an expanded state, said catheter assembly being represented generally by reference numeral 301.

Catheter assembly 301 comprises a medical catheter 303 and an internal bolster 305. Medical catheter 303 is an elongated, tubular structure preferably made of a flexible, biocompatible material, such as silicone rubber. Catheter 303 is shaped to include a cylindrical wall 307 terminating in a first end 309 and in a second end 311, cylindrical wall 307 coaxially surrounding and defining a longitudinal bore 313 adapted to convey fluids, such as food and/or medications, to a patient in need thereof. A series of ruler markings (not shown) are printed on catheter 303 and extend several inches from first end 309 in the direction of second end 311 to facilitate the cutting of catheter 303 to a desired length after catheter 303 has been implanted in a patient.

Internal bolster 305 comprises a pair of identical resilient members 327 collectively forming a reversibly transformable anchor at first end 309 of catheter 303. In the present embodiment, this anchor is in the form of an iris diaphragm; however, the anchor may take forms other than that of an iris diaphragm. Each resilient member 327 is reversibly transformable between a spiral shape, when relaxed, and a straightened shape, when forcibly unfurled. As can be seen, assembly 301 differs notably from assemblies 11, 101 and 201 in that members 327 are oriented relative to catheter 303 so that (i) when each member 327 is in a relaxed state, said member 327 spirals radially outwardly relative to catheter 303 and in a direction away from second end 311 of catheter 303 and (ii) when each member 327 is in an unfurled state, said member 327 extends parallel to the longitudinal axis of catheter 303, with its free end 328 extending in the direction from first end 309 to second end 311.

Assembly 301 additionally differs from assemblies 11, 101 and 201 in that resilient members 327 do not include an embedded wire. Instead, assembly 301 is preferably a unitary structure made entirely of injection molded silicone rubber, said silicone rubber being of sufficient strength for members 327 to retain catheter 303 in a patient.

It should be understood that, although the present embodiment includes two resilient members 327 spaced around first end 309 of catheter 303, there could be more than two resilient members 327 spaced around first end 309 of catheter 303. In addition, it should be understood that resilient members 327 are not limited to assuming, when at rest, the particular spiral shape shown in FIGS. 6(*a*) and 6(*b*). Rather, resilient members 327 may instead form a looser curl, a tighter curl, a longer curl, a shorter curl, a fatter curl, a thinner curl, etc. In addition, there may be alternate geometries to spirals, such as balled or knotted members, that may have improved strength. Moreover, there may be various types of resilient members disposed around the catheter.

Assembly 301 may be implanted in a patient in much the same way as assemblies 11, 101 and 201, the principal difference being that assembly 301 does not require the use of an extraneous delivery device to straighten resilient members 327 during implantation. This is because, due to the direction in which resilient members 327 are coiled, one may simply hold members 327 in an unfurled state against the length of catheter 303 with one's hand while inserting first end 309 of catheter 303 into the patient. Once the free ends of resilient members 327 have entered the patient and are released by the medical professional, they will return to their expanded state on their own.

To remove assembly 301 from a patient, one simply pulls on the external portion of catheter 303 until resilient members 327 unfurl.

It should be understood that, if desired, one could insert a wire into each of the resilient members 327 of assembly 301.

Figure 8:
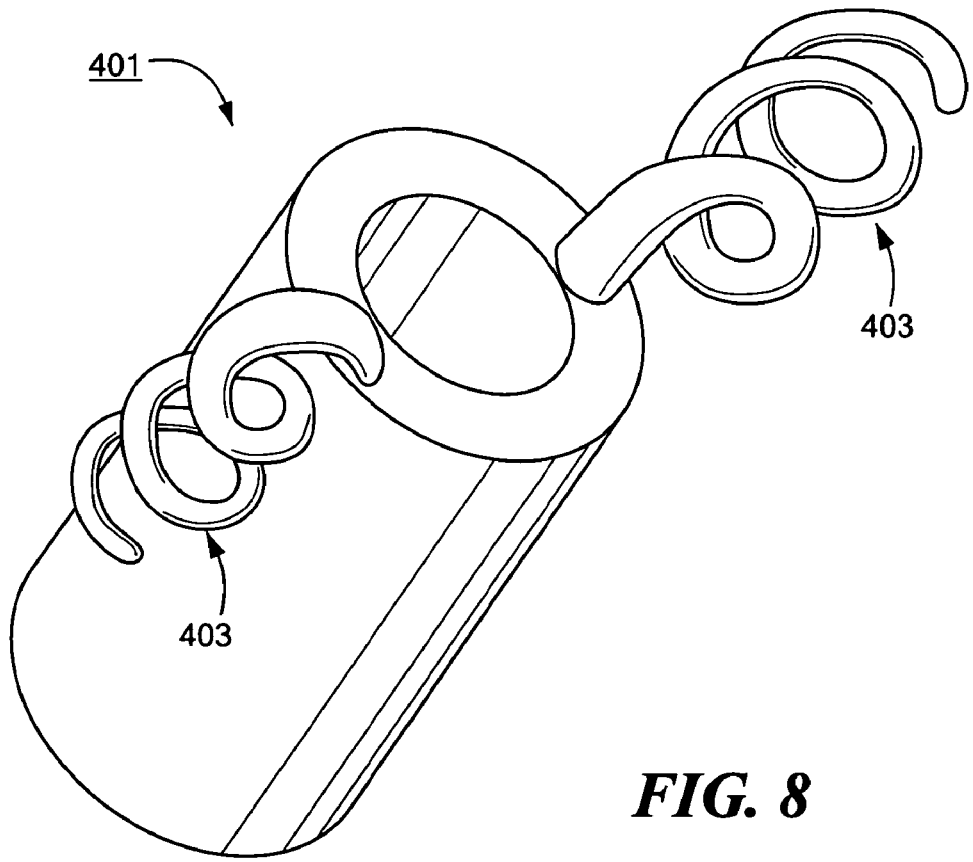
FIG. 8 is a perspective view of a fifth embodiment of a catheter assembly constructed according to the teachings of the present invention, the internal bolster of the catheter assembly being shown in an expanded state.

Referring now to FIG. 8, there is shown a perspective view of a fifth embodiment of a catheter assembly constructed according to the teachings of the present invention, the internal bolster of the catheter assembly being shown in an expanded state, said catheter assembly being represented generally by reference numeral 401.

Catheter assembly 401 is similar in many respects to catheter assembly 11, the principal difference between the two assemblies being that catheter assembly 401 includes resilient members 403, instead of resilient members 27. Resilient members 403 differ principally from resilient members 27 in that resilient members 403, when at rest, assume a coiled shape that is substantially non-planar or three-dimensional (i.e., the coils extends laterally relative to the length of the resilient member) whereas resilient members 27, when at rest, assume a spiral shape that is substantially planar or two-dimensional. It should be understood that, although the present embodiment includes two resilient members 403, there could be more than two members 403. Also, instead of using resilient members 403, one could use other types of resilient members that have three-dimensional shapes to increase the extent of engagement between the resilient members and the patient, examples of such resilient members including spiral-type resilient members that bend laterally or that twist away from the perpendicular.

Assembly 401 may be implanted, used and removed in the same fashion as described above for assembly 11.

In another embodiment (not shown), the resilient members are disposed within the catheter during deployment and, thereafter, are pushed out or pulled out of the catheter to assume their expanded state.

In still another embodiment (not shown), instead of or in addition to the automatic curling of the members forming the anchor, the curling may be effected or locked by means of a filament or the like. Such locking may involve the distal end of the resilient member locking into itself or the catheter.

In still yet another embodiment (not shown), the distal end of the catheter is made to include a plurality of resilient members covered with a sheath. As the sheath is moved proximally relative to the resilient members, the resilient members become uncovered and are allowed to assume their relaxed, curled state. As more of the length of the resilient members is exposed by continued withdrawal of the sheath, the size of the curled resilient members increases.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method for inserting a gastrostomy tube into a patient, comprising:
   inserting a distal end of an endoscope through the patient's mouth into the patient's stomach;
   making an incision in the patient's abdominal wall and stomach from the outside of the patient's body;
   using a catheter assembly comprising: (i) a catheter having a proximal end, a distal end, and a cylindrical wall surrounding a primary longitudinal bore; and (ii) an internal bolster disposed at the distal end of the catheter, the internal bolster comprising a plurality of resilient members collectively forming a reversibly transformable anchor, wherein each of the resilient members has a spiral shape when in a relaxed state and a straightened shape when in an unfurled state, and wherein the spiral shape extends radially outwardly from the catheter and away from the proximal end of the catheter, wherein a first end of each resilient member is free and a second end of each resilient member is fixed to the distal end of the catheter in both the relaxed state and the unfurled state;
   inserting the catheter assembly into the stomach through the incision with the resilient members in the unfurled state without the use of an external delivery device; and
   once the resilient members have entered the patient, allowing the resilient members to return to the relaxed state spiral shape and anchor the catheter assembly in the patient.

2. The method of claim 1, wherein the internal bolster comprises exactly two resilient members.

3. The method of claim 1, wherein the resilient members lie along a length of the catheter when in the unfurled state.

4. The method of claim 1, wherein the spiral shape is substantially two-dimensional.

5. The method of claim 1, wherein the spiral shape is substantially planar.

6. The method of claim 1, wherein the catheter and resilient members form a one-piece molded structure.

7. The method of claim 1, wherein during the step of inserting the catheter assembly, each straightened resilient member extends proximally along the outside of the cylindrical wall of the catheter.

8. The method of claim 1, wherein in the unfurled state, the first end of each resilient member is spaced proximally from the second end of each resilient member.

9. A method for inserting a gastrostomy tube into a patient, comprising:
   inserting a distal end of an endoscope through the patient's mouth into the patient's stomach;
   making an incision in the patient's abdominal wall and stomach from the outside of the patient's body;
   using a catheter assembly comprising: (i) a catheter having a proximal end, a distal end, and a cylindrical wall surrounding a primary longitudinal bore; and (ii) an internal bolster disposed at the distal end of the catheter, the internal bolster comprising a plurality of resilient members collectively forming a reversibly transformable anchor, wherein each of the resilient members has a spiral shape when in a relaxed state and a straightened shape when in an unfurled state, and wherein the spiral shape extends radially outwardly from the catheter and away from the proximal end of the catheter, wherein the catheter and the resilient members form a unitary structure made entirely of silicone rubber;
   inserting the catheter assembly into the stomach through the incision with the resilient members unfurled without the use of an external delivery device; and once the resilient members have entered the patient, allowing the resilient members to return to the spiral shape and anchor the catheter assembly in the patient.

10. The method of claim 9, wherein the resilient members lie along a length of the catheter when in the unfurled state.

11. The method of claim 9, wherein the spiral shape is substantially two-dimensional.

12. The method of claim 9, wherein the spiral shape is substantially planar.

13. The method of claim 9, wherein the catheter and resilient members form a one-piece molded structure.

14. The method of claim 9, wherein during the step of inserting the catheter assembly, each straightened resilient member extends proximally along the outside of the cylindrical wall of the catheter.

15. The method of claim 9, wherein in the unfurled state, a free end of each resilient member is spaced proximally from a fixed end of each resilient member.

* * * * *